(12) United States Patent
Cathala et al.

(10) Patent No.: US 9,217,171 B2
(45) Date of Patent: Dec. 22, 2015

(54) COLORIMETRIC DEVICE FOR DETECTING, IN AN AQUEOUS SOLUTION OF INTEREST, HYDROLYTIC ENZYMATIC ACTIVITY WITH REGARD TO AT LEAST ONE POLYMER OF INTEREST

(75) Inventors: Bernard Cathala, La Chapelle sur Erdre (FR); Carole Cerclier, La Chapelle sur Erdre (FR)

(73) Assignee: INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 0 days.

(21) Appl. No.: 13/808,861

(22) PCT Filed: Jul. 6, 2011

(86) PCT No.: PCT/FR2011/051613
§ 371 (c)(1),
(2), (4) Date: Jan. 7, 2013

(87) PCT Pub. No.: WO2012/004536
PCT Pub. Date: Jan. 12, 2012

(65) Prior Publication Data
US 2013/0115643 A1 May 9, 2013

(30) Foreign Application Priority Data
Jul. 7, 2010 (FR) ...................................... 10 55529

(51) Int. Cl.
| | | |
|---|---|---|
| C12Q 1/34 | (2006.01) | |
| G01N 33/52 | (2006.01) | |
| G01N 21/45 | (2006.01) | |
| G01N 21/78 | (2006.01) | |
| A61K 38/00 | (2006.01) | |
| G01N 21/77 | (2006.01) | |

(52) U.S. Cl.
CPC ........... *C12Q 1/34* (2013.01); *G01N 21/45* (2013.01); *G01N 21/78* (2013.01); *G01N 2021/7779* (2013.01)

(58) Field of Classification Search
None
See application file for complete search history.

(56) References Cited

U.S. PATENT DOCUMENTS

| | | | |
|---|---|---|---|
| 5,611,998 | A | 3/1997 | Aussenegg et al. |
| 8,722,437 | B2 * | 5/2014 | Bocking et al. ................. 438/29 |
| 2004/0062682 | A1 | 4/2004 | Rakow et al. |
| 2007/0297944 | A1 * | 12/2007 | Wendland et al. ............. 422/56 |
| 2010/0068749 | A1 * | 3/2010 | Bauer et al. ...................... 435/29 |
| 2010/0279394 | A1 * | 11/2010 | Bocking et al. ............ 435/287.1 |

FOREIGN PATENT DOCUMENTS

| | | |
|---|---|---|
| EP | 0677738 | 10/1995 |
| WO | WO 2004/031760 | 4/2004 |

OTHER PUBLICATIONS

Habibi et al "Langmuir—Blodgett films of cellulose nanocrystals: Preparation and characterization" Journal of Colloid and Interface Science 2007 316 388-397.*
Ducere et al. "A capacitive humidity sensor using cross-linked cellulose acetate butyrate" Sensors and Actuators B 2005 106 331-334.*
Junghanns et al. "Nanocrystal technology, drug delivery and clinical applicationsInternational Journal of Nanomedicine" 2008:3(3) 295-309.*
Cunningham—et al. (2002) A plastic colorimetric resonant optical biosensor for multiparallel detection of label-free biochemical interactions, Sensors and Actuators B Chemical ., vol. 81, pp. 316-328.*
Ducere et al. (Apr. 5, 2005) "A Capacitive Humidity Sensor Using Cross-Linked Cellulose Acetate Butyrate," *Sensors and Actuators B*. 106(1):331-334.
Habibi et al. (Nov. 5, 2007) "Langmuir-Blodgett Films of Cellulose Nanocrystals: Preparation and Characterization," *J. Colloid Interface Sci.* 316(2):388-397.
International Preliminary Report on Patentability corresponding to International Application No. PCT/FR2011/051613, mailed Sep. 8, 2011.
International Search Report and Written Opinion corresponding to International Application No. PCT/FR2011/051613, mailed Sep. 8, 2011.
Nelson et al. (1944) "A Photometric Adaptation of the Somogyi Method for the Determination of Glucose," *J. Biol. Chem.* 153:375-380.
Yokota et al. (Feb. 7, 2007) "Surface Morphology of Cellulose Films Prepared by Spin Coating on Silicon Oxide Substrates Pretreated with Cationic Polyelectrolyte," *Applied Surface Science*. 253(9):4208-4214.

* cited by examiner

*Primary Examiner* — Anand Desai
*Assistant Examiner* — Samuel Liu
(74) *Attorney, Agent, or Firm* — Lathrop & Gage LLP

(57) ABSTRACT

This invention concerns a colorimetric device for detecting, in an aqueous solution of interest, a hydrolytic enzymatic activity with regard to at least one polymer of interest.
This device (1) includes (i) a substrate (2) and (ii) a transparent detection layer (3), including the said polymer of interest. This detection layer (3) is adapted so that, on the one hand, after application of the said aqueous solution of interest, when it is deprived of said hydrolytic enzymatic activity, it preserves the said first thickness e, and on the other, after the application of the said aqueous solution of interest, when it includes the said hydrolytic enzymatic activity, it has a second thickness e', thinner than the said first thickness e,
and the said first thickness e and/or the said second thickness e' of the said detection layer (3) are adapted to generate a color by an optical interference phenomenon caused by the recombining of the light beams reflected at the interfaces (4, 5) of the said detection layer (5).

19 Claims, 3 Drawing Sheets

COLORIMETRIC DEVICE FOR DETECTING, IN AN AQUEOUS SOLUTION OF INTEREST, HYDROLYTIC ENZYMATIC ACTIVITY WITH REGARD TO AT LEAST ONE POLYMER OF INTEREST

CROSS-REFERENCE TO RELATED APPLICATIONS

This application is a U.S. National Stage application of international application PCT/FR2011/051613, filed on Jul. 6, 2011, which designates the United States, which was published in French, and which claims the benefit of FR1055529, filed Jul. 7, 2010. Each of these applications is incorporated by reference herein in its entirety.

The present invention relates to a device for detecting, in an aqueous solution of interest, hydrolytic enzymatic activity with regard to at least one polymer of interest, advantageously of the biopolymer type.

PRIOR ART

In many technical and industrial fields, the identification and study of enzymes having a hydrolytic activity regarding polymers represent a major challenge.

For example, such hydrolytic enzymes like are an essential tool for generating biofuels from the biomass, rich in ligno-cellulose elements.

More specifically, the vegetal wall is a complex structure comprising intermingled polymers (cellulose, hemicellulose, lignin, pectin, etc.); hydrolytic enzymes are advantageously used to break down the cellulose chains into sugars intended to be fermented to create bioethanol.

For this purpose, it is interesting to use technical devices which allow the detection, in a fast, simple and reliable way, the hydrolytic activity of an enzyme of interest, or a combination of enzymes of interest, with respect to a polymer or a combination of polymers.

In particular, dedicated colorimetric devices are often implemented, using chemical reactions to reveal the enzymatic activity. To achieve this, these chemical colorimetric devices use colorants or chemical detection indicators.

For instance, one chemical method classically used for dosing the activities of hydrolases polysaccharides is known under the name of "Nelson's method" (described in particular in Nelson et al., J. Biol. Chem. 1944, 153, 375-380).

Colorimetric devices, for detecting hydrolytic activity relative to one or several polymers, are often complex to use, require many manipulations and reagents, and generally require the use of a reading device (for instance a spectroscope).

To detect the presence of an analyte in a medium of interest, some colorimetric devices use a well-known optical phenomenon: the interference.

These devices comprise for that at least one thin transparent film or one thin transparent layer, applied to a supporting substrate.

The thickness of this thin transparent film is included within a range of values permitting a particular colour to appear due to the interference optical phenomenon, also known as an "interferential colour" or "interference colour".

An explanation for this phenomenon derives from the fact that part of the incident beam is reflected on the air/thin film interface, while another part of the incident beam is refracted then reflected on the second thin film/substrate interface.

The reflected beams interact to create an optical interference phenomenon consisting in combinations between the light waves which are either constructive interferences or destructive interferences.

The resulting colour corresponds to the wavelength at which the phenomenon of constructive interference is maximum.

For instance, a device of this type is described in the document WO-A-2004/031760, intended in particularly to detect organic vapours.

The corresponding device includes, for this purpose, three superimposed layers:—a reflecting substrate,—a detecting layer able to absorb the analyte and change of optical thickness upon exposure to the analyte and—an upper semi-reflective layer.

In practice, the analyte of interest attaches to the detection layer by adsorption after passing through the reflector substrate by porosity. This phenomenon causes a change in the thickness of this detection layer and, as a corollary, a change in its interferential colour.

Such a device allows for detection of an analyte because of the fixing of the latter to the detection layer; this device and its implementation process allow detection of an analytic type.

The device according to the document WO-A-2004/031760 is not intended to detect analytes according to their biological activities.

In addition, this device of the prior embodiment is in no way designed for, or even suited to, the implementing of the functional detection of an enzymatic activity within a solution of interest. In particular, the upper semi-reflective layer may constitute an obstacle to the eliminating of the detection layer, in particular by rinsing, subject to degradation by an enzyme.

Accordingly, there is a need for such colorimetric devices, using an optical interference phenomenon on a thin detection layer, able to detect, in an aqueous solution of interest, hydrolytic enzymatic activity with respect to at least one polymer of interest.

The document US-A-2010/068749 describes such a colorimetric device to analyze the age and/or quality of certain natural products, for instance, foodstuffs.

This colorimetric device consists of a superimposition of layers, that is, a support, a reflector, a biodegradable polymer layer and a mirror.

This colorimetric device is configured so that changing of the thickness of the biodegradable polymer layer causes a change of colour visible to the naked eye, thus depicting the presence of an enzymatic activity.

For this purpose, the biodegradable polymer layer is made of a polymer which is degradable by biomolecules, especially by enzymes or catalytic metabolites; the mirror consists of a layer of nanoparticles.

However, this colorimetric device is not fully satisfactory; and this particular superimposition of layers, in particular the presence of the mirror layer based on nanoparticles, is relatively complex to manufacture.

SUMMARY OF THE INVENTION

In this context, the applicant has developed a colorimetric device capable of detecting hydrolytic enzymatic activity in an aqueous solution of interest, with respect to at least one polymer of interest, simply, quickly and particularly sensitive.

For this purpose, the device according to the invention is based on using a thin transparent layer (or thin transparent film) forming an interference filter for the detection of enzymatic activity.

This detection layer is capable of producing an interferential colour, which is modified, appearing or disappearing according to the case, on exposure to an aqueous solution comprising the desired hydrolytic enzymatic activity.

For this purpose, this colorimetric device according to the invention is characterized by the fact that it comprises (i) a substrate delimited by at least one upper surface, and (ii) a transparent detection layer having a first thickness e and including the said polymer of interest. The transparent detection layer includes, on the one hand, an upper surface to which it is intended to apply the said aqueous solution of interest and forming an initial air/detection layer interface, and on the other, a lower surface formed on the said upper surface of the substrate, together forming a second detection layer/substrate interface. Said two interfaces are liable to generate an optical reflection phenomenon.

The detection layer is adapted so that, on the one hand, after application of the said aqueous solution of interest, when it is deprived of the said hydrolytic enzymatic activity, it preserves the said first thickness e, and on the other, after the application of the said aqueous solution of interest, when it includes the said hydrolytic enzymatic activity, it has a second thickness e', thinner than the said first thickness e, And the said first thickness e and/or the said second thickness e' of the said transparent detection layer are adapted to generate a colour by an optical interference phenomenon generated by recombining the light beams reflected on the said air/detection layer and detection layer/substrate interfaces.

According to a preferred embodiment, the first thickness e of the detection layer is chosen to generate a first colour by an optical interference phenomenon; and the detection layer is adapted so that, on one hand, after application of the said aqueous solution of interest, when it is deprived of the said hydrolytic enzymatic activity, the said first thickness e generating the said first colour is preserved, and, on the other hand, following the application of the said aqueous solution of interest when it includes the said hydrolytic enzymatic activity, to present a second thickness e', thinner than first thickness e, producing either a second colour by an optical interference phenomenon, different from the said first colour, or causing the said first colour to disappear.

Other advantageous features of the invention which may be considered as a combination or independently of each other are specified below:
- the first thickness e of the transparent detection layer is a uniform thickness chosen from a range of thicknesses extending from 70 to 900 nm, and preferably between 75 and 250 nm;
- the first thickness e and/or the second thickness e' of the said transparent detection layer are adapted to generate a colour by an optical interference phenomenon with a maximum reflectance at a wavelength included between 380 nm and 780 nm, and preferably between 400 nm and 700 nm;
- the refraction index $n_c$ of the transparent detection layer is included between 1.2 and 1.7, and preferably between 1.4 and 1.6;
- the polymer contained in the upper detection layer is chosen from the biopolymers, that is advantageously from oligosaccharides, polysaccharides, peptides, proteins, lignins, nucleic acids, cutin and/or suberin.

According to a particular embodiment, the substrate is transparent and the transparent detection layer has a refraction index $n_c$ differing from the substrate refraction index $n_s$.

In this case, the refraction index $n_s$ of the substrate is advantageously higher than the refraction index $n_c$ of the transparent detection layer.

According to an alternative embodiment, the substrate is opaque and has a reflective upper surface.

According to yet another characteristic of the invention, the polymer contained in the transparent detection layer is preferably immobilized to withstand the application of the solution of interest deprived of enzymatic activity.

In this case, the upper detection layer advantageously contains nanocrystals forming hydrogen cross-linking networks (hornification) with the polymer of interest.

Preferably, the nanocrystals consist advantageously of polysaccharide nanocrystals and preferably of cellulose nanocrystals.

The corresponding nanocrystals advantageously have a negative surface charge. And the transparent detection layer consists of at least two first sub-layers each containing the polymer of interest; the said first sub-layers being separated in pairs by an interposed sub-layer containing a poly-cationic compound.

In one particular embodiment, the transparent detection layer consists of at least one pair of two sub-layers (preferably at least two pairs of two interposed sub-layers) each containing at least one polymer of interest, with a first sub-layer comprising a first or several first polymers of interest (advantageously polysaccharide nanocrystals), and a second sub-layer containing a second or several second polymers of interest.

Again, in this case and as an alternate, the transparent detection layer advantageously contains a resin forming covalent cross-linking networks with the polymer of interest This invention also concerns a process for detecting, in an aqueous solution of interest, hydrolytic enzymatic activity with regard to at least one polymer of interest.

This process is characterized in that it includes at least the following succession of steps:
- the supply of a colorimetric device as defined above,
- the application of the said aqueous solution of interest to the upper surface of the transparent detection layer,
- the washing of the said upper surface of the transparent detection layer to eliminate the aqueous solution of interest,
- the drying of the said transparent detection layer, and
- the analysis of the colour of the said transparent detection layer at the application site of the said solution of interest.

This invention also concerns the use of a colorimetric device as defined above for detecting, in an aqueous solution of interest, hydrolytic enzymatic activity with regard to at least one polymer of interest.

DESCRIPTION OF FIGURES

This invention is further illustrated, without being limited in any way by the following description related to the attached figures.

DETAILED DESCRIPTION OF THE INVENTION

Figure 1:
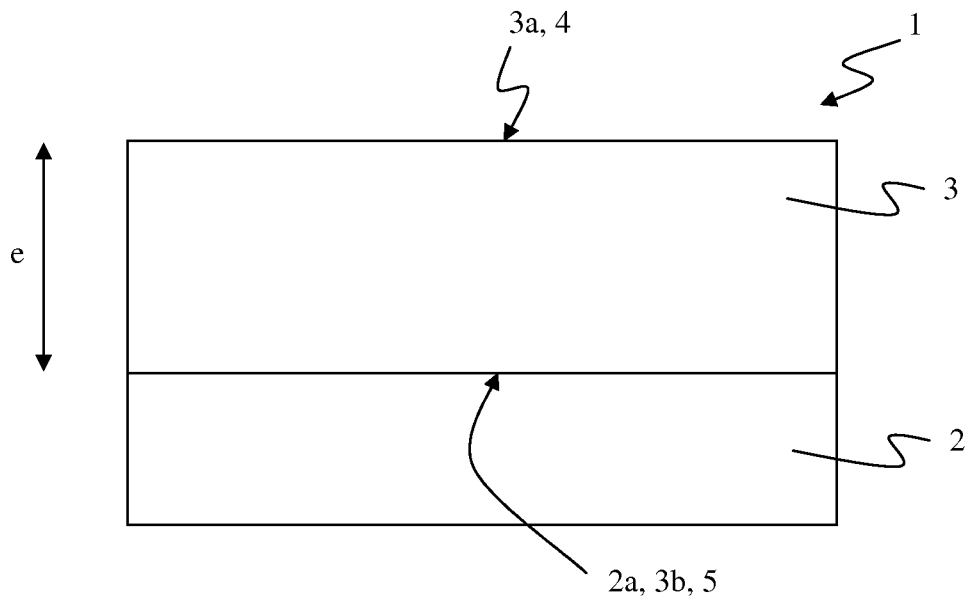
FIG. 1 is a schematic and elevation view of a colorimetric device according to the invention before the application of the aqueous solution of interest.

This invention thus concerns a colorimetric device for detecting, in an aqueous solution of interest, a hydrolytic enzymatic activity with regard to at least one polymer of interest.

The term "detection" refers to the discrimination between the presence and the absence of the hydrolytic enzymatic activity in the aqueous solution of interest.

In an alternate or complementary manner, the "detection" of the hydrolytic enzymatic activity consists in determining a quantitative enzymatic activity value in the aqueous solution of interest.

This "quantitative value" can be expressed in katal (kat) that is the quantity of enzyme which catalyzes the transformation of 1 mole of substrate per second.

This "quantitative value" can also be expressed:
  as "International Unit" (IU) corresponding to the quantity of enzyme which catalyzes the transformation of 1 µmole of substrate per minute,
  as "number of rotations" (kcat), which is the number of substrate molecules transformed per enzyme molecule per second (or the number of substrate moles transformed per enzyme mole),
  as "molar activity" which is the number of substrate moles transformed per enzyme mole per minute,
  as "specific activity", or the activity per milligram of enzyme protein expressed in IU/mg enzyme protein (or µkat/mg).

The term "detection" refers further to the discrimination between the presence and the absence of the active enzyme containing the said hydrolytic enzymatic activity in the aqueous solution of interest.

"Hydrolytic enzymatic activity" refers to a mechanism implemented by an enzyme of the hydrolase type catalyzing a biochemical hydrolysis reaction.

The enzymes liable to implement hydrolysis reactions like this are grouped together in particular in the EC 3 group of the nomenclature known as "EC" (standing for "Enzyme Commission numbers"—"Nomenclature Committee of the International Union of Biochemistry and Molecular Biology (NC-IUBMB)").

Among the enzymes of the hydrolase type, reference can be made to enzymes having a hydrolytic activity regarding biopolymers.

Among these enzymes capable of hydrolyzing biopolymers, in particular, mention can be made of hydrolase polysaccharides known also as hydrolase glycosides or glycosidases (these enzymes are favourably classified in group EC 3.2.1).

The term "hydrolase polysaccharides" refers for instance to xylanases, cellulases, chitinases, pectinases, mannases, and Cellulyve (registered trademark).

Among the biopolymer hydrolytic enzymes mention might also be made, for instance, of proteases, nucleases, and ligninases.

The "aqueous solution of interest" consists of a liquid phase containing several chemical species, that is at least (i) a solvent essentially consisting of water, preferably entirely by water, and (ii) one or several compounds in a solution or in suspension, called "solution(s)".

At least one of the said compounds, in a solution or a suspension, consists of an active enzyme capable of generating the said hydrolytic enzymatic activity for aqueous solutions comprising the said activity.

Examples of polymers with respect to which an enzymatic activity is desired are listed below.

The colorimetric device 1 according to the invention is shown schematically in FIG. 1.

This colorimetric device 1 comprises two superimposed layers that are (i) a substrate 2, serving as a support and delimited by an upper surface 2a, and (ii) a transparent detection layer 3, comprising the polymer of interest and having a refraction index designated as "$n_c$".

Generally speaking, in this description, the refraction indices given apply to a temperature of 20° C. and a wavelength of 520 nm.

The transparent detection layer 3 is delimited by two opposing surfaces: (i) an upper surface 3a, to which it is intended to apply the said aqueous solution or solutions of interest and (ii) a lower surface 3b, formed on the said upper surface 2a of substrate 2.

The upper surface 3a of the transparent detection layer 3 is advantageously free in that it is not covered in any way by an additional layer (for example a layer of nanoparticles).

The distance between these two surfaces 3a and 3b of the detection layer 3 defines the thickness of the said transparent detection layer 3. This transparent detection layer 3 initially includes an initial thickness referred to as "e" (FIG. 1).

Together, these layers 2 and 3 form two optical interfaces respectively at the upper surface 3a and the lower surface 3b of the detection layer 3, that is:
  a first interface 4, situated between the air and the detection layer 3 (forming a dioptre), and
  a second interface 5, between the detection layer 3 and the substrate 2.

According to the invention, the transparent detection layer 3 is adapted to permit the detection of a hydrolytic enzymatic activity with respect to the polymer or polymers of interest, in an investigated aqueous solution. This detection layer 3 is a means for translating the said detected hydrolytic enzymatic activity into an optical signal.

Figure 2:
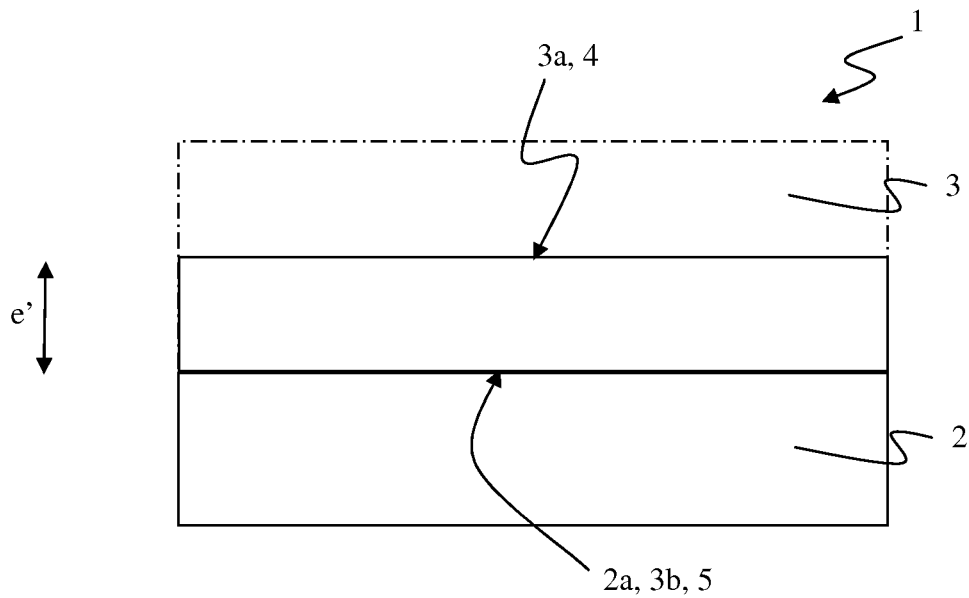
FIG. 2 shows the colorimetric device according to FIG. 1, after the application of an aqueous solution of interest comprising a hydrolytic enzymatic activity.

For this purpose, the transparent detection layer 3 is adapted so that, after the application of the said aqueous solution of interest, when it is deprived of the said hydrolytic enzymatic activity, it preserves the said initial thickness e (FIG. 1). The same transparent detection layer 3 is also adapted so that, after application of the aqueous solution of interest, when it includes the said hydrolytic enzymatic activity, it has a second thickness e', thinner than the said initial thickness e (FIG. 2).

Accordingly, the presence of a hydrolytic enzymatic activity in the aqueous solution of interest is able to cause a reduction in the thickness of the detection layer 3 (from the initial thickness e to the second thickness e'), resulting in a change of the observable coloration (directly by an operator or using an appropriate device) in this transparent detection layer 3. To achieve this, the initial thickness e of the transparent detection layer 3 and/or the second thickness e' of the transparent detection layer 3 are able to generate a colour by an optical interference phenomenon.

As developed in the following, these properties of the device 1 will allow an optical change to be observed in the detection layer 3 in the presence of an enzymatic activity of interest.

Advantageously, this optical change consists in one of the following phenomena: (i) the change from a first interferential colour to a second interferential colour, or (ii) the appearance of an interferential colour, or (iii) the disappearance of an interferential colour.

Indeed, the transparent detection layer 3 acts as an interference fitter. Depending on its thickness e or e', the transparent detection layer 3 takes on a colour due to the optical reflection and interference phenomena (constructive/destructive) for some particular wavelengths, advantageously in the visible range.

More specifically, when the light meets the first interface 4 (air/detection layer 3), part of the beam is reflected. The other part of the light is transmitted through the detection layer 3 where it is reflected from the second interface 5 (detection layer 3/substrate 2).

The beam reflected from the second interface 5 covers a longer distance, causing the phase shifting of the light. When the distance covered is on the order of magnitude of half the wavelength of the incident light, the recombination of the reflected beams causes interference leading to the appearance of a colour at detection layer 3.

Indifferently, reference is made to the "interference colour" or the "interferential colour" which can be observed at the detection layer 3.

The term "colour" in reference to the detection layer 3, especially an interferential colour, applies to a colour perceived (advantageously, directly by an individual by the "naked eye"), having (i) achromatic tone (the chromatic tone characterizes the colour itself), that is, red, green, yellow, blue etc.) and/or (ii) a clarity and/or (iii) a saturation.

The term "colour", especially an interferential colour, also applies to the wavelength in which the phenomenon of constructive interference is maximum; this colour may also correspond to the wavelength where the reflectance curve is maximum, advantageously in the visible domain; this colour can also be defined by its spectral curve (reflectance depending on wavelength).

The interference, and accordingly the appearance of the colour, is therefore related essentially (i) to the thickness of the detection layer 3 and (ii) to the reflection phenomena at the two interfaces 4, 5 delimiting the said detection layer 3. This colour does not require any chemical marking of the polymer.

In practice and as mentioned above, depending on the first thickness e and the second thickness e' of the detection layer 3, this change of colouring consists advantageously in the appearance, disappearance or change of the interferential colour in the detection layer 3.

This "change of colouring" then consists advantageously in a change of (i) the chromatic tone and/or (ii) the clarity and/or (iii) the saturation, observable directly by an individual.

To be complete, various aspects of the colorimetric device 1 are described in detail below.

Substrate

The substrate 2 is made of material capable (i) of forming a support for the transparent detection layer, and (ii) of ensuring reflection (total or partial and advantageously specular) of the light beams applied to the colorimetric device 1.

According to a first embodiment, the substrate 2 consists of a transparent material having a refraction index designated as "$n_s$". Advantageously, this material is of the isotropic homogeneous linear medium type.

The refraction index $n_s$ of this substrate 2 differs from the refraction index $n_c$ of the transparent detection layer 3. The second interface 5 between the detection layer 3 and the substrate 2 thus forms a dioptre.

In particular, the component material of the substrate 2 is chosen with a refraction index $n_s$ higher than the refraction index $n_c$ of the transparent detection layer 3.

For instance, for an upper detection layer 3 having a refraction index $n_c$ included between 1.2 and 1.7, the substrate 2 advantageously consists of a slice of silicon (commonly named "wafer") having a refraction index included between 3 and 5.

Generally speaking, the greater the difference between the refraction indices $n_c/n_s$ of this interface 5 is (between the detection layer 3 and the substrate 2), the higher the reflection coefficient (percentage of reflected light) will be.

In a second embodiment, the substrate 2 consists of an opaque material having an upper surface 2a with reflecting properties.

Here, "reflecting" refers to total optical reflection or at least semi-reflection.

Materials suitable for obtaining an upper reflecting surface 2a like this include chemical metallic elements such as aluminium, chrome, gold, nickel, and silicon, silver or a mixture of them. Other suitable materials include metallic oxides such as chrome oxide and titanium oxide.

Generally speaking, and whatever the embodiment, the reflection coefficient at the second interface 5 is, for instance, at least 20%, possibly included between 20% and 90%, and may even be greater than 90%.

Transparent Detection Layer

The detection layer 3 comprises at least one polymer of interest, that is, a single polymer or a combination of polymers.

The term "polymer" includes copolymers and homopolymers.

The polymer is advantageously chosen from among the biopolymers or in other words, the "organic polymers", that is polymers derived from a biological edifice.

For information, these polymers can be chosen from among:
  oligosaccharides and polysaccharides (cellulose, xylane, pectin, chitosan, chitin, xyloglucane, arabinoxylan, etc.),
  peptides and proteins (bovine or human albumin serum, glutenin, etc.),
  nucleic acids, in particular desoxyribonucleic acids, ribonucleic acids, etc.),
  cutin, suberine and lignin.

Biopolymers like this can occur in an isolated form (that is, distinct polymer chains), aggregated form (that is intermingled polymer chains) or crystallized (that is, polymer chains organized according to an orderly repetitive pattern).

The detection layer 3 has a refraction index $n_c$ which is advantageously included between 1.2 and 1.7, and preferably between 1.4 and 1.6;

The upper surface 3a and the lower surface 3b of the detection layer 3 are parallel, or at least approximately parallel to one another.

These two surfaces 3a and 3b are preferably plane, or at least approximately plane.

As mentioned above, these two surfaces 3a and 3b define the first thickness e, which advantageously consists of a uniform or constant thickness over the entire surface.

This first thickness e is chosen advantageously in a field included between 70 and 900 nm, and again preferably included between 75 and 250 nm.

As indicated previously, the transparent detection layer 3 is capable of preserving the said first thickness e on the application of a solution deprived of the said enzymatic activity.

To this end, the polymer or polymers of interest are advantageously immobilized.

This immobilization can be generated by cross-links (i) of the covalent or "chemical" type (shrinkage) and/or (ii) of the non covalent or "physical" type (electrostatic, hydrogen, Van der Waals force).

In case (i) above, the upper detection layer 3 advantageously contains a resin forming covalent cross-linked networks with the polymer or polymers of interest.

This resin is chosen depending on the polymer or polymers to be reticulated.

For choosing and implementing such a resin, the following document could be used as a reference, for example: Ducéré et al., 2005 ("A capacitive humidity sensor using cross-linked cellulose acetate butyrate" Sensors and Actuators B: Chemical 106 (1), 331-334 (2005)), Wu et al., 2009 ("Molecularly imprinted organic-inorganic hybrid membranes for selective separation of phenylalanine isomers and its analogue" Separation and Purification Technology 68 (1), 97-104 (2009)), and Schuler et al., 2001 ("Decomposable hollow biopolymer-based capsules" Biomacromolecules 2 (3), 921-926 (2001)).

For instance, reticulation by melamine-urea-formaldehyde resins (also known as "MUF") offers the following advantages:
 - the reticulating reaction can occur with many chemical functions (alcohol, amine, phenol), allowing a great number of biopolymer classes to be reticulated;
 - there are water soluble resin formulations allowing simple implementation by a mixture of the solution to be applied;
 - reticulation is simple: the monomer is stable at ambient temperature, and it reacts when the film is brought to 90° C. in a dry atmosphere for one hour, this treatment being compatible with most biopolymers.

In case (ii) above, immobilization can be obtained by nanocrystals forming hydrogen cross-linked networks (also referred to as a phenomenon of "hornification") with the polymer of interest.

To do this, the nanocrystals advantageously consist of compounds containing negative electrostatic charges at the surface. For this purpose, it is preferable to choose polysaccharide nanocrystals, and preferably cellulose nanocrystals.

Such nanocrystals are prepared, for instance, by the acid hydrolysis of cotton using the protocol described in Revol et al. (Int. J. Biol. Macromol. 1992, 14, 170-172.) or Cranston et al. (Biomacromolecules, vol 7, 2006, p 2522).

For instance, to stabilize a transparent detection layer 3 based on xyloglucane, cellulose nanocrystals are added. A transparent detection layer 3 based on arabinoxylan is actually fixed advantageously using a melamine-urea-formaldehyde resin.

In addition, the detection layer 3 can consist of a single layer forming an isotropic homogenous linear medium (or "IHLM"). In this case, the detection layer 3 is advantageously made up of the polymer or polymers of interest to its full height.

Alternatively, the transparent detection layer 3 can comprise several superimposed sub-layers, with at least one of the said sub-layers containing the polymer or polymers of interest.

In the latter case, the sub-layer containing the polymer or polymers of interest advantageously forms at the least the upper surface 3a of the detection layer 3.

The detection layers 3 then include advantageously at least two sub-layers, and again advantageously, between 8 and 16 sub-layers.

In this arrangement, the detection layer 3 advantageously consists of several pairs of superimposed sub-layers, advantageously between four and eight pairs of superimposed sub-layers. The said pairs of superimposed sub-layers are identical, or at least approximately identical, to one another.

In such a structure with several sub-layers, the detection layer 3 can include an alternation of polymers of interest, forming pairs of superimposed sub-layers with, for instance, successively one sub-layer of cellulose (advantageously in the form of nanocrystals) and one sub-layer of xyloglucane.

In another example, the detection layer 3 can include an alternation of sub-layers forming pairs of superimposed sub-layers with, successively, one sub-layer of polyelectrolyte (for instance poly-L-lysine or "PLL", or poly(allylamine) hydrochloride or "PAH") and one sub-layer containing the polymer or polymers of interest (for instance, a mixture of cellulose and xyloglucane).

The alternation of the sub-layers, in particular, makes it possible to achieve thickness e as desired for the detection layer 3, as developed below with respect to the process of deposit.

Furthermore, in the case of a substrate 2 and a detection layer 3 having the same electrostatic charge, the upper face 2a of the substrate 2 is advantageously lined with an attaching sub-layer consisting of a polyelectrolyte (represented for instance in FIG. 3 and designated by reference number 7b), to form a cross-link interface between the said substrate 2 and the said detection layer 3.

For instance, the polyelectrolyte sub-layer consists of poly-L-lysine or of poly(allylamine) hydrochloride. This is the case advantageously, on the one hand, for a substrate consisting of a silicon wafer and on the other, for a detection layer or sub-layer containing cellulose nanocrystals, both of which are negatively charged.

Manufacturing Process

The transparent detection layer 3 is deposited on the substrate 2 by an appropriate technique, in one or several steps.

Generally speaking, there are different techniques for constructing the transparent detection layer 3.

The dip-layering technique (or "dip-coating") consists in dipping the substrate into a solution of polymers. This method produces very fine layers a few nanometers thick.

To implement this technique, reference could be made into the following documents: Jean et al., 2008 (Structural Details of Cellulose Nanocrystals/Polyelectrolytes Multilayers Probed by Neutron Reflectivity and AFM Langmuir 24 (7), 3452-3458 (2008)), or Cranston et al., 2006 ("Morphological and Optical Characterization of Polyelectrolyte Multilayers Incorporating Nanocrystalline Cellulose" Biomacromolecules 2006, 7, (9), 2522-2530).

Spray-layering (or "spray-coating") consists in spraying the polymer onto the support. The solvent is partly evaporated during spraying and the remainder evaporates after deposit. This technique has the advantage of being faster than dip-layering.

This technique is described, for instance, in the document by Wagberg et al. "The Build-Up of Polyelectrolyte Multilayers of Microfibrillated Cellulose and Cationic Polyelectrolytes" Langmuir 24 (3), 784-795 (2008).

Centrifugal layering (or spin-coating) consists in a depositing the solution containing the polymer on the substrate, preferably at its centre. The rotating substrate causes the solution deposited on the surface to spread and evacuates excess liquid by spinning; the residual solvent evaporates leaving only the material on the substrate. The thickness of the thin film obtained varies with the speed of rotation, the viscosity and/or the concentration of the solution.

This last technique is studied, for instance, in the documents by Cranston et al., "Morphological and Optical Characterization of Polyelectrolyte Multilayers Incorporating Nanocrystalline Cellulose" Biomacromolecules 2006, 7, (9), 2522-2530, or Cranston et al, "Birefringence in Spin-Coated Films Containing Cellulose Nanocrystals" Colloids and Surfaces A 2008, 325, (1-2), 44-51.

In the framework of the last technique, to adjust the thickness of the layer or the sub-layers designed to form the detection layer 3, it is possible to refer advantageously to the following formula (1), obtained from David et al., "Spin Coating of Thin and Ultrathin Polymer Films" Polymer engineering and science, vol. 38, No. 12, December 1998, p 2040, i.e.:

$$h_f \propto \left(\frac{\eta_0}{\rho\omega}\right)^{1/2} \tag{1}$$

Where
$h_f$: thickness of layer
$\eta_0$: initial viscosity of solution
$\rho$: liquid density
$\omega$: spinning speed This principle is particularly valid for polyelectrolytes but also applies to any materials having other types of interactions with each other.

In practice, the detection layer 3 is advantageously applied in several steps to form a superimposition of sub-layers. A procedure like this is developed, for instance, in the Example section below.

With this approach, the manufacturing and stability of the detection layer 3 can be optimized. Such an approach can also be useful for adding sub-layers to the thickness, aiming at defining the final thickness e' of the detection layer 3, after enzymatic action.

Process for Detecting Enzymatic Activity

In practice, the process for detecting, in an aqueous solution of interest, hydrolytic enzymatic activity with regard to at least one polymer of interest, comprises at the least the following succession of steps After the supply of a colorimetric device 1 as defined above in conjunction with FIG. 1, the aqueous solution of interest is applied to the upper surface 3a of the transparent detection layer 3.

This aqueous solution is deposited as a drop whose volume is preferably included between 20 μL and 1 mL.

The colorimetric device 1 is then incubated for an appropriate time and under appropriate conditions, depending in particular on the enzymatic activity being studied.

The upper surface 3a of the transparent detection layer 3 is then washed to eliminate the aqueous solution of interest and eliminate part of the detection layer which may have gone through enzymatic hydrolysis.

To do this, it is preferable to use an aqueous solution deprived of enzymatic activity, for instance water, or an appropriate dissolution buffer.

The said transparent detection layer 3 is then dried.

To finish, the colour of the transparent detection layer 3 is analyzed in the application site of the said solution of interest.

To do this, a light source (or a light beam) is directed towards the transparent detection layer 3.

This light source may be natural or artificial. This light is preferably of the polychromatic type, and again, preferably, of the continuous spectrum type.

Unless stipulated otherwise, the colorimetric device 1 is observed at a normal angle to the upper surface 2a of the substrate 2. Other viewing angles could be used, for instance less than 30°, and preferably again, less than 15°, with respect to an axis perpendicular to the upper surface 2a of the substrate 2.

As mentioned previously, if there is no hydraulic enzymatic activity in the aqueous solution of interest, the transparent detection layer 3 preserves the initial thickness e. In this case there is no optical change in the detection layer 3.

Conversely, the presence of a hydrolytic enzymatic activity in the aqueous solution of interest causes degradation of the transparent detection layer 3, resulting in a decrease of its thickness.

In this case, the transparent detection layer 3, initially having a first thickness e (FIG. 1), finishes at a second thickness e' (FIG. 2) which is thinner than the said first thickness e.

This second thickness e' is advantageously included between 0 (the detection layer 3 is eliminated) and 250 nm, and preferably between 70 and 250 nm.

This change of thickness from the first thickness e to the second thickness e', advantageously causes one of the following optical changes:

(i) a change from an initial interferential colour to a second interferential colour the said interferential colours being different from each other, (ii) a change from an absence of interferential colour until the appearance of an inferential colour or (iii) a change from an interferential colour until the said interferential colour disappears.

The colour of the detection layer 3 can be read (i) directly by the operator or (ii) by means of a suitable reading system.

The change of colour of the transparent detection layer 3 is best observed in the field of visible light and can thus be detected by an individual without using a reading device.

In this case, first thickness e and/or second thickness e' of the detection layer 3 are chosen to obtain an interferential colour whereof the maximum reflectance is situated at a wavelength included between 380 nm and 780 nm, and preferably included between 400 nm and 700 nm.

More generally, the optical change advantageously consists in a change of chromatic tonality, facilitating the reading and interpretation of the results.

To facilitate this reading made directly by an operator, a reference aqueous solution can also be applied to the same detection layer 3, near the application site of the aqueous solution of interest. This reference aqueous solution advantageously consists of an aqueous solution deprived of enzymatic activity (for instance, by inactivation of the enzymatic activity, advantageously over heat).

A different colour between the application site of the solution of interest and the application site of the reference aqueous solution indicates the presence of enzymatic activity in the said solution of interest. And identical colour between the application site of the solution of interest and the "reference" site indicates the absence of any enzymatic activity in the solution of interest.

If necessary, reading devices can be used to observe a change of colour in the transparent detection layer, especially when the colorimetric device is exposed to other light sources, such as ultraviolet (UV) rays, infrared rays or near infrared rays.

For that, reading devices may be used for an analysis of the colorimetric devices 1, for instance photodetectors, including in Charge-Coupled Devices (CCD), digital cameras, etc.

In this case, colorimetric device 1 is used in an automated colorimetric system advantageously including an optical reading device, a light source and optionally, means for analyzing the colour change.

Enzymatic activity can then be sought for by comparing the colours obtained (i) by the solution of interest and by a "reference" solution or (ii) before and after the application of the aqueous solution of interest.

In this case, reading devices are a means of advantageously determining the visible reflectance spectrum in the detection layer 3. In an advantageous manner and as an example, it can be considered that there is an optical change when the maximum reflectance wavelength in said detection layer 3 is different (i) between the solution of interest and the "reference" solution or (ii) before and after the application of the aqueous solution of interest.

A different colour before and after the application of the aqueous solution of interest demonstrates the presence of enzymatic activity in the said solution of interest. An identical or approximately identical colour, before and after the application of the aqueous solution of interest demonstrates the absence of enzymatic activity in the said solution of interest.

In addition, to determine a quantitative value for the enzymatic activity in the aqueous solution of interest, it is simply necessary to adapt, for instance, the dilutions of the solution of interest and/or the incubation time and/or the structure of the detection layer. It can then be considered that the final colour depends on the said quantitative value.

Particular Embodiment Modes

In a first embodiment corresponding to FIG. 1, the transparent detection layer 3 advantageously consists of an isotropic homogenous linear medium (or "IHLM") deposited in one or several steps.

In this case, the decreased thickness of the detection layer 3 (from initial thickness e in FIG. 1 to the final thickness e' in FIG. 2) depends essentially on the incubation time.

Figure 3:
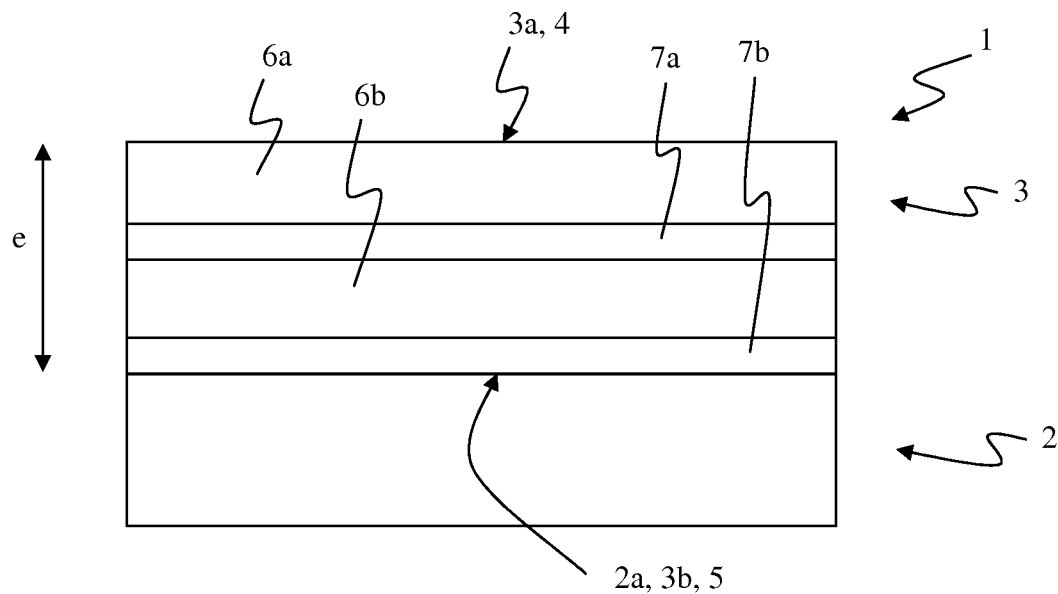
FIG. 3 is a schematic and elevation view of a colorimetric device comprising a thin detection layer consisting of several sub-layers, before the application of the aqueous solution of interest.

In an alternative manner and as shown in FIG. 3, the transparent detection layer 3 can consist of a superimposition of four sub-layers 6 and 7:
two of the sub-layers 6a and 6b each comprise the polymer or polymers of interest, advantageously immobilized by anionic nanoparticles, and
two other sub-layers 7a and 7b, each contain a polycationic compound.

Each sub-layer 6, 7 forms an isotropic homogenous linear medium (or "IHLM").

These sub-layers 6 and 7 are deposited alternatingly, forming pairs of superimposed sub-layers 6a, 7a and 6b, 7b, in particular with a sub-layer of polymer(s) 6 forming the upper surface 3a of the detection layer 3.

This structure is aimed especially at overcoming the difficulties of obtaining thick individual sub-layers; the alternation of the sub-layers makes it possible to obtain the desired initial thickness e.

For instance, the polycationic sub-layers 7 consist of poly (allylamine) hydrochloride or poly-L-lysine.

In this case, the decreased thickness of the detection layer 3 (from initial thickness e in FIG. 3 to final thickness e' in FIG. 4) depends advantageously on the sub-layer of polymer(s) 6a forming upper surface 3a of the detection layer 3.

Figure 4:
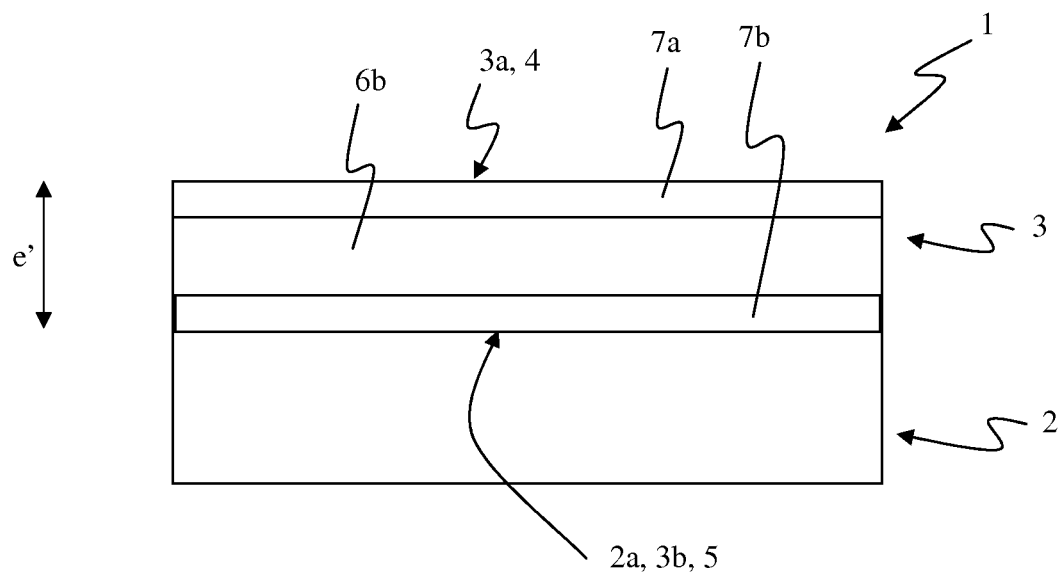
FIG. 4 shows the colorimetric device according to FIG. 3, after the application of an aqueous solution of interest comprising a hydrolytic enzymatic activity.

In other words, the hydrolytic enzymatic activity preferably ensures total degradation of the sub-layer of polymer(s) 6a initially forming the upper surface 3a of the detection layer 3 (as shown in FIG. 4). After this enzymatic action, the upper surface 3a of the detection layer 3 consists of the upper surface of the directly underlying polycationic sub-layer 7a.

This embodiment has the advantage of allowing the testing of initial thickness e as well as the final thickness e' generated in the presence of enzymatic activity.

Again, as an alternative and in conformity with FIG. 3, the transparent detection layer 3 can comprise a superimposition of sub-layers 6 and 7:
two of the sub-layers 6a and 6b each have the first or several first polymers of interest and
two other sub-layers 7a and 7b, each contain the second or several second polymers of interest.

These sub-layers 6 and 7 are deposited alternatively, forming superimposed pairs of sub-layers 6a, 7a and 6b, 7b.

For instance, the first polymer of interest consists of cellulose nanocrystals; and the second polymer of interest consists of xyloglucane.

Generally speaking, the colorimetric device according to the invention can thus be adapted to detect hydrolytic activities with respect to a polymer of interest.

The advantage of this device is (i) that it does not need complex equipment for its use, (ii) that it has a high miniaturization potential and (iii) that it can be integrated into a high rate analysis system.

It is also worth considering that it can be used for the semi-quantitative measurement of a hydrolytic activity, by adapting more particularly the thickness of the detection layer and the reaction time.

For instance, one possible process for the semi-quantitative measurement of this kind of hydrolytic activity in an aqueous solution could include advantageously the following steps:
the supply of a colorimetric device according to the invention, whose transparent detection layer consists of at least one polymer of interest suitable to undergo hydrolysis in the presence of the said hydrolytic activity,
the application of the said aqueous solution of interest to the upper surface of the said transparent detection layer of said colorimetric device,
the washing of the said upper surface of the transparent detection layer,
the drying of the said transparent detection layer, and
the analysis of the colour of the said transparent detection layer at the said application site of the said solution of interest, and comparison to one or several reference sites (for instance, a calibration range), for the semi-quantitative evaluation of hydrolytic activity in this said aqueous solution.

This colorimetric device according to the invention also offers the advantage of allowing the identification of specific hydrolytic activity with respect to a determined polymer.

For instance, one possible process for the identification of this kind of specific hydrolytic activity in an aqueous solution includes advantageously the following steps:
the supply of a colorimetric device according to the invention whose transparent detection layer consists of at least one polymer of interest suitable to undergo hydrolysis in the presence of the said hydrolytic activity,
the application of the said aqueous solution of interest to the upper surface of the said transparent detection layer of said colorimetric device,
the washing of the said upper surface of the transparent detection layer,
the drying of the said transparent detection layer, and the analysis of the colour of the said transparent detection layer at the application site of the said solution of interest, and the comparison of the colour of the said application site with a reference site, to determine the presence or absence of the said hydrolytic activity, the positive selection of the said aqueous solution or of the enzyme or enzymes it contains, if comparison reveals that the said tested aqueous solution suitably modifies the colour of the said transparent detection layer.

This invention is also illustrated by the examples developed below.

EXAMPLES

Example 1

Producing a Transparent Detection Layer on a Substrate and Study of its Stability Equipment The various products used include:

high viscosity wheat arabinoxylan (AX-HV), 47 cSt (sold by Megazyme)

medium viscosity wheat arabinoxylan (AX-MV), 22 cSt (sold by Megazyme)

poly(allylamine hydrochloride (PAH) (sold by SIGMA)

cellulose nanocrystals (C) (also referred to as whiskers), prepared by the acid hydrolysis of cotton using the procedure described in Cranston and al (Biomacromolecules, vol 7, 2006, p 2522)

xyloglucane (XG) extracted from tamarind seed (Silvestre Virginie, 2004 thesis, Nantes University), melamine formaldehyde resin (MUF) Resimene AQ-7550 (sold by INEOS Melamines); this resin is first diluted to 10% from a commercial solution of 640 µL and made up to 5 mL of HCl at $10^{-2}$ mol/L, a silicon wafer the upper surface of which is polished.

Methods 1.1. Producing Thin Layers 1.1.1. Construction by Spin-Layering

The support is cleaned in a corrosive mixture consisting of 70% sulphuric acid $H_2SO_4$ and 30% hydrogen peroxide $H_2O_2$ for 30 minutes.

The support is then rinsed in two successive baths of water and dried in nitrogen.

The layers are produced by the spin-layering device SPIN 150 NPP (SPS Europe) at a rotation speed of 2000 RPM with identical acceleration for all the tests of 1400 rpm per second.

1.1.2. Cellulose/Xyloglucane Layer

The cellulose/xyloglucane layers are designed to detect cellulolitic activities. It is known that xyloglucane and cellulose are sensitive to cellulases (they have the same skeleton structure).

The silicon wafer is put into the spin-layering device.

The PAH (0.5 g/L) is placed at the centre of a silicon wafer and left to stand for 5 min.

The silicon wafer is put into rotation for 1 minute at the chosen speed, then rinsed in water for 1 minute.

Then, the cellulose/xyloglucane solution containing 5 g/L of cellulose nanocrystals and 5 g/L of xyloglucane is placed at the centre and left to stand for 5 min. The xyloglucane and the cellulose nanocrystals are capable of setting up noncovalent interactions which can generate a network able to immobilize the mixture after drying.

The silicon wafer is then put into rotation for 3 minutes and rinsed for 3 minutes.

These steps are repeated a second time to obtain a film with two pairs of sub-layers (one PAH sub-layer—one sub-layer of a cellulose/xyloglucane mixture).

1.1.3. Arabinoxylan Films (AX)

The arabinoxylan films were produced either with resin (10 and 15 g/L of AX), or without resin (5, 10 and 15 g/L of AX).

The preparation of a 15 g/L arabinoxylan solution with 5% of resin, for instance, is obtained as follows: 3.75 mL of arabinoxylan at 20 g/L are taken and 37.5 µL of resin at 10% are added; the mixture is made up to 5 mL with ultrapure water. The added volume of resin is adjusted to suit the desired concentration (5, 10, 15 and 20%).

Solutions containing 10 g/L of arabinoxylan are made up from solutions at 15 g/L according to the principle described above.

In practice, the PAH solution is placed at the centre of a silicon wafer and left to stand for 5 min. Then, the silicon wafer is put into rotation for 3 minutes and rinsed in water for 3 minutes. Finally, the arabinoxylan solution is placed at the centre, left to stand for 5 minutes and put into rotation for 3 min.

1.2. Thickness Measurement by Interferometer

To measure the thickness of the surfaces deposited on the silicon wafers, a UV-visible Specord S600 spectrophotometer is used.

The silicon wafer is deposited on a support in front of two mirrors. The light is reflected from the first mirror, transmitted to the sample then reflected to the second mirror and retransmitted to the detector.

Film thickness measurement by reflected light is a well-known technique based on the interaction of the film with light. It depends on interferences resulting from partial reflection and transmission at the various interfaces.

The spectra are recorded throughout the range of wavelengths covered by the spectrophotometer (from 182 nm to 1019 nm).

The acquisition of the spectra and the calculation of the film thicknesses use the WinAspect software.

1.3. Stability Tests

First of all, the silicon wafer on which the polymer is deposited is immersed in water then dried.

Secondly, the strength of the detection layer is tested using (i) a saline solution to evaluate the effect of the ionic force (NaCl at 0.1 mol/L), and (ii) of acid and basic solutions (HCl with pH 2 and NaOH with pH 12) to evaluate the effect of the pH.

A drop of each solution is placed on the substrate and left to stand for three minutes.

The device is rinsed in water then dried.

The detection layers are photographed at each step of the stability test.

Results: Stability of Detection Layers

To be efficient, the thin layers must be consistent and stable in the absence of enzymes. The detection layers must also be rinsed with water and be stable in the studied aqueous solutions.

A distinction is made between two cases:

cellulose/xyloglucane mixtures: the films are stable without the addition of reticulating agent; therefore, we tested only the effect of ionic force and pH on the thin layers.

Arabinoxylans: the films are not stable alone (simple washing with water is sufficient to cause the colour to disappear because of the low cohesion of the polymer chains in the layers)

The addition of formaldehyde/urea resin has been tested to stabilize the detection layer based on arabinoxylan with respect to the pH and the ionic force; the quantity of resin needed was then optimized.

2.1. Cellulose/Xyloglucane

During a stability test drops of NaCl (0.1 mol/L), HCl (pH 2) and NaOH (pH 12) are each deposited on the detection layer and left there for three minutes; the detection layer is then rinsed with water.

It is observed that the surface does not change colour before and after the test.

Accordingly, the dual layer of cellulose and xyloglucane is stable with respect to the tested media.

2.2. Arabinoxylan

The influence of several parameters was investigated concerning the stability of the arabinoxylan layers: the type of arabinoxylan (high viscosity (HV) and medium viscosity (MV)), the concentration (15 g/L and 10 g/L) and the percentage of reticulated resin in the arabinoxylan solution (between 5 and 20%).

2.2.1. Effect of Type of Arabinoxylan

Before running the stability test under harsh conditions, the layers were bathed in water.

For this purpose, arabinoxylan layers with medium viscosity at 15 g/L and 10 g/L are studied with resin at 20%. After bathing them in water, we observed that the layers remain homogenous.

The arabinoxylan layers with high viscosity at 15 g/L and 10 g/L are then studied with resin at 20%. After bathing them in water, a colour change is observed which may be due to decreased thickness and be linked to a loss of polymer. In addition, it is observed that these layers are less homogenous than the medium viscosity arabinoxylan layers.

Therefore, the high viscosity arabinoxylan layers are not stable. This could be linked to the fact that the molecules form aggregates since the molecular density of arabinoxylan is high. This makes it difficult for the resin to reticulate.

2.2.2. Effect of Resin Concentration and Percentage on Layers Stability

In the light of the previous results, tests are run on medium viscosity arabinoxylan layers constructed at a spin speed of 2000 rpm and from concentration solutions of 10 and 15 g/L.

To determine the stability of the layer, we use two parameters: ionic force and pH (acid and basic).

Solutions of NaCl at 0.1 mol/L, HCl at pH2 and NaOH at pH12 were deposited on the thin layers in the same way.

Since the xylanase is diluted in the acetate buffer, it is necessary to check whether the buffer degrades the polymer layer. This acetate buffer is therefore tested on the arabinoxylan layers too.

Stability tests were run on medium viscosity arabinoxylan films at 15 g/L and 10 g/L, for various resin concentrations (5%, 10%, 15% and 20%).

A colour change is observed at the location of the deposits, in particular for 5%, 10% and 15% resin concentrations. This colour change is less visible when the resin percentage increases.

In the rest of the study, the layers concerning us must be stable enough for not to be rinsed in a solution but allow enzymatic activity to be displayed.

To address these two criteria, it is advisable to choose layers containing 15% resin.

The medium viscosity arabinoxylan layers at 15 g/L are stable for a 20% resin percentage and the arabinoxylan layers at 10 g/L are stable for 15 and 20 resin percentages.

We observed that for the two medium viscosity samples of arabinoxylan at 15 g/L and 10 g/L, there is a persisting blemish corresponding to the acid solution, whatever the resin concentration. It could be due to the fact that the arabinoxylan has hydrolyzed in the presence of acid. It means that we must take precautions, and use the enzyme in a low acid medium.

It is noteworthy that the acetate buffer does not degrade the thin layer. This means that the enzyme can therefore be diluted in an acetate buffer at pH 5, the optimum condition for the enzyme.

2.3. Conclusion

The cellulose/xyloglucane layer is stable in the presence of salt, with an acid pH and an alkali pH.

The high viscosity arabinoxylan layers are not homogenous after being bathed in water whereas the medium viscosity arabinoxylan films are stable.

It is observed that the blemishes are less visible as the resin concentration increases on medium viscosity layers of arabinoxylan. Therefore, it is decided to continue the study with medium viscosity arabinoxylan films with 15% resin.

Similar tests also revealed stability for 24 hours.

Example 2

Measurement of Enzymatic Activity

The detection of enzymatic activity by devices derived from Example 1 above is compared with the conventional "Nelson" method.

The enzymes studied below consist of:
β-xylanase M1 (8000 U; 216 U/mg; 2300 U/mL; sold by Megazyme), and
cellulyve, derived from a *Trichoderma Reesei* which has not been totally purified (theoretical activity is 4880 nkat/g, 49 mg/g) (sold by Lyven).

1. Nelson Method

With the Nelson method, the reducing ends liberated during the hydrolysis of a polysaccharide are dosed by an enzyme. Dosing is indirect: in an alkaline medium and at boiling point, the pseudo-aldehydic grouping of the reducing ends reduces the cupric ions into cuprous ions. The latter react with the arsenio-molybdic reagents to produce a blue colouring whose optical density (OD) varies linearly with the quantity of reducing oses. The number of ends is dosed after 10 minutes of incubation.

Nelson dosing takes place in two stages:
determination of a calibration line defining the response of the method according to the concentration at the reducing ends; this step is carried out on monomer sugars (glucose and xylose).
dosing of enzyme activities that we will be studying on polymers in solution: we will measure the activities of a xylanase and a cellulase on arabinoxylans and on xyloglucane respectively.

1.1.—Equipment
Solution A:
200 g $Na_2SO_4$ anhydrous
25 g $Na_2CO_3$ anhydrous
25 g Tartrate double Na—K
20 g $NaHCO_3$ anhydrous
Solution B:
30 g $CuSO_4$, $5H_2O$
4 drops $H_2SO_4$ concentrated
$H_2O$ qsf 200 mL
Solution C: 25 mL of solution A+1 mL of solution B
Solution D:
50 g $(NH_4)_6MO_7O_{24}$, $4H_2O$ dissolved in 800 mL $H_2O$
42 mL $H_2SO_4$ concentrate poured in quickly
6 g $Na_2HAsO_4$, $7H_2O$ dissolved in a little water
$H_2O$ qsp 1 L 1.2. Preparation of Standard Ranges Prepare a mother solution of the ose at 250 µg/mL.

In this case, use a glucose mother solution as a reference for the xyloglucane. The xylose mother solution will be the reference for the two high and medium viscosity arabinoxylan solutions.

Various mother solution dilutions will be produced between 0 and 250 µg/mL. The optical density is measured for each concentration to obtain a standard range.

1.3. Dosing Enzymatic Activities:

Enzymatic Reaction

To prepare the specimens, put 135 µL of the mother solution and 15 µL of the enzymatic solution in a tube and incubate them at 40° C. for 10 minutes.

After 10 minutes, the enzymatic activity is stopped by adding 100 µL of a sample to 100 µL of solution C.

The white reference is used for measuring the OD when the enzyme is deactivated. The white reference consists of 100 µL of solution C, to which we add 10 µL of enzyme and 90 µL of the mother solution.

Colorimetric Reaction

The samples are put in a boiling water bath for 15 minutes.

The samples are then cooled and solution D is added (100 µL) to obtain different colours between the white and the samples.

The plates are constantly stirred for 10 minutes then 1 mL of water is added.

To finish, 250 µL from each well is transferred into a plate with 96 wells for reading the optical density on a plate reader at 600 nm.

To express the results, the concentration of the standard range must be expressed in µmol.

The following formula (1) is used for calculating the activity:

$$a = \text{Delta}DO/\text{slope} \times 150/15 \times 1000/t \times dil \quad (1)$$

Where:
a: enzymatic activity in nkat/mL
DeltaDO: optical density difference between sample and white
The slope is expressed in µmol
150 is the total volume of the rectional medium
15 is the volume of the enzyme test amount
t is the incubation time in s (for this experiment t=600 s)
dil is the dilution of the enzyme on which the enzymatic reaction was produced The variation of the minimum acceptable OD for the measurement to be valid is 0.1.

Formula (2) used for calculating the minimum activity is as follows:

$$\text{Delta}(a) = \text{Delta}(\text{Delta}DO)/\text{slope} \times 150/15 \times 1000/t \quad (2)$$

The calculation was made for standard ranges of xylose and glucose.

On the basis of these results, it can be deduced that the lowest measurable activity using this method is 3 nkat/mL.

2. Evaluation of Enzymatic Activity on Detection Layer a drop of the enzymatic solution to be tested and a drop of the reference solution (1 mL of the enzymatic solution diluted and heated to 110° C. for one hour) are applied to the detection layer for three minutes.

The devices according to the invention are rinsed in water and dried.

The detection layers are photographed at each step of the enzymatic test.

The first test is performed with an enzymatic solution at 125 µg/mL (0.6 nkat/mL) for the cellulyve, and the solution is diluted to 2000th for the xylanase (19 nkat/mL).

We then dilute the enzymatic solutions until the enzymatic activity is no longer visible on the surfaces.

3. Results 3.1. Nelson Method

Calibration Line

We first set up two ranges of standards for determining the relation between the measured optical density and the concentration at the reducing ends.

The standard range of the glucose is the reference for the xyloglucane; the standard range of the xylose is the reference for the arabinoxylan.

The calibration lines make it possible to calculate the activity of the enzyme by determining the number of liberated reducing ends (therefore the breaks made by the enzyme) in a determined period of time.

Measurement of Cellulyve Activity

We investigated the activity of the Cellulyve on the xyloglucane. The cellulyve derives from a *Trichoderma Reesei*, a fungus which is capable of secreting a large amount of cellulose enzymes.

We prepared a mother solution of cellulyve at 0.5 mg/mL with theoretical activity of approximately 2.4 nkat/mL.

From the calibration lines, we determine an enzymatic activity of 7 nkat/mL. This result differs slightly from the theoretical activity but is of the same order of magnitude.

Measurement of Xylanase Activity

We verified the activity of the xylanase on two substrates: high and medium viscosity arabinoxylans.

The activity of the pure xylanase, as submitted by the supplier, is estimated at approximately 38 000 nkat/mL.

We calculated the activity of the pure xylanase based on the results obtained for solutions diluted to 2000th and 1000th.

The results obtained are shown in table 1 below.

TABLE 1

| | Activity of xylanase as measured in nkat/mL | Activity of pure xylanase as measured in nkat/mL |
|---|---|---|
| AX-HV | | |
| Dilution to 1000th | 32 | 31 889 |
| Dilution to 2000th | 16 | 31 943 |
| AX-MV | | |
| Dilution to 1000th | 33 | 32 828 |
| Dilution to 2000th | 19 | 37 080 |

We encounter a value of approximately 32 000 nkat/mL, which is of the same order of magnitude as the value given by the supplier.

3.2. Enzymatic Activity on Detection Layers

Cellulose/Xyloglucane

As developed above in Example 1, the cellulose/xyloglucane detection layer is formed by sub-layers of a mixture of cotton cellulose nanocrystals (Ct) and xyloglucane (XG), deposited alternatingly with the sub-layers of poly(allylamine) hydrochloride (PAH).

The layer obtained has a total thickness of 175 nm and is a pale yellow colour.

Initially, we use the same concentration of Cellulyve as used for Nelson's method (125 µg/mL, or 0.6 nkat/mL).

A drop of the enzymatic solution is deposited (0.6 nkat/mL) and a drop of the inactivated enzyme is also deposited (reference: 1 mL of the diluted enzyme solution heated to 110° C. for one hour).

After the depositing of a drop of cellulase, rinsing and drying, a blue colour appears where the enzyme was deposited, suggesting that the layer thickness has been decreased.

Figure 5:
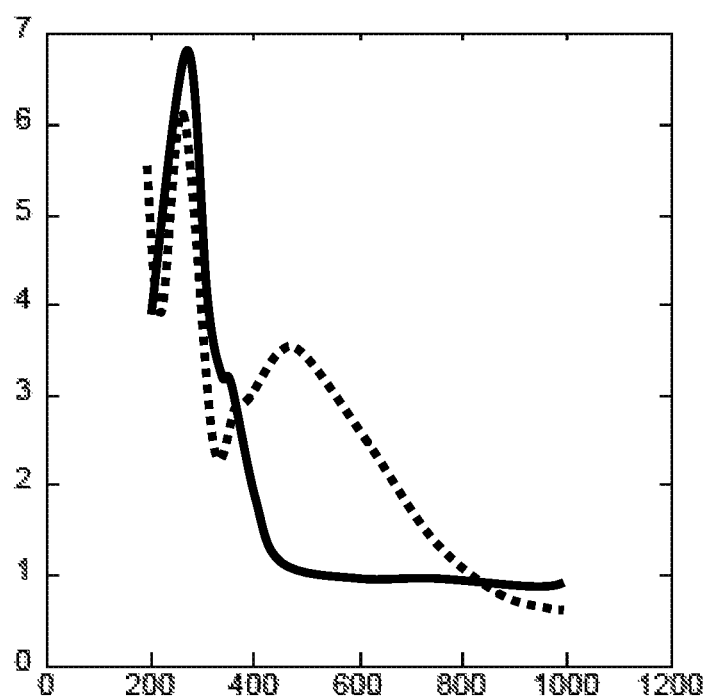
FIG. 5 represents the interference curves, before (dotted line) and after (solid line) degradation, for a detection layer based on cellulose and xyloglucane; these curves correspond to the reflectance depending on the wavelength in nm.

This decreased thickness was confirmed by interferometry and by atomic microscopy. The measurement of the interference profile (FIG. 5), before and after the action of the enzyme, clearly reveals that the phenomenon of interference at the origin (before the action of the enzyme) has disappeared due to the action of the enzyme. This result indicates that the thickness of the detection layer is less than 150 nm.

Although the layer is unchanged after washing with water, its thickness has decreased considerably due to the action of the enzyme. Note that the roughness of the layer after the action of the enzyme remains remarkably low. It would appear that, although there is no theory to confirm it, (i) either the enzyme works by the erosion of the layer without penetrating into the structure, (ii) or the PAH forms a barrier to the action of the enzyme.

Here, it can be seen that this device is liable to be an opportunity for studying the action of the enzyme with respect to solid substrates. This device should also make it possible to reconstruct a model system in a heterogeneous medium.

Then, the enzyme is diluted several times to determine the enzymatic activity detection threshold. The studied solutions are presented in table 2 below.

TABLE 2

| Name of solution | Dilution | Enzymatic activity |
| --- | --- | --- |
| S1 | 1/40th | 0.06 nkat/mL |
| S2 | 1/400th | $6 \cdot 10^{-3}$ nkat/mL |
| S3 | 1/4000th | $6 \cdot 10^{-4}$ nkat/mL |
| S4 | 1/40 000th | $6 \cdot 10^{-5}$ nkat/mL |

In practice, we see that the more we dilute (from S1 to S4), the less the colour change is significant compared to the original colour. Accordingly, the more we dilute, the less the polymer film is degraded.

The minimum activity which can be detected visually after 3 minutes is 0.06 nkat/mL (S1).

But Nelson's method makes it possible to detect a minimum activity of 3 nkat/mL. Tests on the device according to the invention are therefore 20 times more sensitive than Nelson's method.

Furthermore, Nelson's method requires an incubation time of 10 minutes whereas the test according to the invention needs only 3 minutes. This also proves that the method according to the invention is faster.

Arabinoxylan (HV-MV)

Here again, we use the same enzyme concentration as in Nelson's method (xylanase diluted to $1/2000^{th}$ or 19 nkat/mL)

A drop of enzymatic solution (19 nkat/mL) and an inactivated enzyme (reference) are deposited on the arabinoxylan films at 15 g/L (blue colour) and 10 g/L (grey-brown colour).

We then see that after incubation and rinsing, the colour disappears where the enzyme was deposited whereas the colour remains unchanged on the reference site.

In the same way as for the layers based on cellulose and xyloglucane, we effectively detect enzymatic activity.

For arabinoxylan at 10 g/L, the enzymatic activity is less visible because the initial colour of the detection layer (grey-brown) is relatively similar to that of the silicon wafer. There is little or even no change in the level of the chromatic tonality.

Then, other tests are performed with a dilution of the enzyme to determine the minimum detection threshold. The studied solutions are presented in table 3 below.

TABLE 3

| Name of solution | Dilution | Enzymatic activity |
| --- | --- | --- |
| S1 | 20 000th | 1.9 nkat/mL |
| S2 | 200 000th | 0.19 nkat/mL |
| S3 | $2 \cdot 10^6$th | $1.9\ 10^{-2}$ nkat/mL |
| S4 | $2 \cdot 10^7$ht | $1.9\ 10^{-3}$ nkat/mL |

We first investigate the various dilutions of xylanase which worked on the medium viscosity arabinoxylan films at 15 g/L and 10 g/L.

On the medium viscosity film of arabinoxylan at 15 g/L, the colour disappears when the activity of the enzymatic solution is 1.9 nkat/mL (S1). A change of colour is still distinguished for enzymatic activity of up to $1.9.10^{-2}$ nkat/mL (S3).

Therefore, the test on the arabinoxylan is 150 times more sensitive than Nelson's method.

The medium viscosity arabinoxylan film thickness at 10 g/L is less than that of the arabinoxylan films at 15 g/L, and the enzymes degrade more easily the arabinoxylan films at 10 g/L.

For the medium viscosity arabinoxylan films at 10 g/L, the colour change is less visible than on the arabinoxylan films at 15 g/L. This is due to the fact that the thickness of the arabinoxylan films at 10 g/L is lesser and the colour is closer to that of the silicon wafer.

4. Conclusion

The activities of the enzymes determined by Nelson's method correspond to the activities given by the suppliers.

For testing on devices according to the invention, we have used the same enzyme concentrations as it used for Nelson's method. Enzymatic activity was indeed observed.

Dilutions were made to determine the detection threshold of enzymatic activity by means of a device according to the invention.

The results obtained demonstrate that the device according to the invention will detect enzymatic activities 20 to 150 times lesser than measured by Nelson's method, and in three times less time.

Example 3

Enzymatic Activity Detection

Equipment

Complementary tests on enzymatic activity detection were run on devices including a detection layer deposited according to a protocol detailed in Example 1.

An initial device used, hereinafter referred to as (PAH-05/XG1)$_4$, includes a blue detection layer consisting of 4 pairs of sub-layers with each pair of sub-layers consisting of:
 a sub-layer of PAH deposited at a concentration of 0.5 g/L, and
 a sub-layer consisting of a mixture of cellulose nanocrystals and xyloglucane deposited respectively at concentrations of 5 g/L and 1 g/L.

The present detection layer has an initial thickness estimated at 160 nm.

A second device used, hereinafter referred to as (C5/XG1)$_8$, also includes a blue detection layer consisting of 8 pairs of sub-layers with each pair of sub-layers consisting of:

a sub-layer of cellulose nanocrystals deposited at a concentration of 5 g/L, and
a sub-layer of xyloglucane deposited at a concentration of 1 g/L, and The present detection layer has an initial thickness estimated at 90 nm.

The studied enzyme consists of a mixture of Cellulyve TR enzymes from the Lyven Company, consisting of a mixture of several cellulases, whose initial activity is 4880 nkat/g.

This enzyme solution was tested at different concentrations on these two devices, respectively 0.6 nkat/mL, 0.24 nkat/mL, 0.12 nkat/mL, 0.06 nkat/mL, 0.024 nkat/mL and 0.006 nkat/mL.

Results

The drops of enzymatic solutions at different concentrations are deposited on the detection layers which are put into an oven at 50° C. for 3, 5, 10 and 15 min.

The appearance of the films $(C5-XG1)_8$ and $(PAH-C5/XG1)_4$ is compared before and after the enzymatic sensitivity test. Activity is detected when the colour of the detection layer is modified.

For the samples $(C5-XG1)_8$, we observe at various times:
  at 3 min, the detected activities of those at 0.6, 0.24 and 0.12 nkat/mL; the surface of the silicon wafer is visible at 0.6 nkat/mL.
  at 5 min, the activity at 0.06 nkat/mL is discernible, and the substrate surface is affected for activities at 0.6 and 0.24 nkat/mL.
  at 10 min, the activity at 0.06 nkat/mL is clearly visible and the surface is affected for the first three concentrations.
  at 15 min, the enzymatic activity is detected for every concentration making the wafer surface visible for the 4 first concentrations; the activity at 0.024 nkat/mL forms a blue blemish.

For the samples $(PAH-C5-XG1)_4$, we observe at various incubation times:
  at 3 min, the detected activities are those at 0.6 and 0.24 nkat/mL.
  at 5 min, the activity at 0.12 nkat/mL is also detected.
  at 10 min, activity at 0.024 nkat/mL is also discernible.
  at 15 min, the attack concentration of 0.024 nkat/mL is still visible.

The visual tests clearly reveal that the action of the enzymes depends on time.

Indeed, for the samples $(C5-XG1)_8$, with high enzymatic activity levels, or at lower activity levels but for longer incubation times, the surface of the silicon wafer is visible.

In addition, blemishes of intermediate colours (light blue or dark blue) appear when the time and/or concentrations to not allow attack through to the silicon wafer.

For the samples $(PAH-05/XG1)_4$, at every concentration and time, the colouring obtained after enzymatic attack is a more or less intense blue.

Therefore, the attack is to the entire thickness of the films $(C5-XG1)_8$, revealing the surface of the silicon wafers as early as 3 min. However, for the samples $(PAH-05/XG1)_4$, the attacks appear to stop at the same level of depth with the dark blue colour corresponding to a thickness of 120 nm, equivalent to 3.5 dual layers of PAH-05/XG1, or the thickness after the depositing of PAH.

According to these results, and although not linked by any theory, it appears possible that the attack of the enzymes on the films $(PAH-05/XG1)_4$ is stopped by the layer of PAH. The PAH apparently acts as a barrier to the enzymes which only attack the cellulose and the xyloglucane, and are unable to reach the surface of the silicon wafers in the same way as for the films $(C5-XG1)_8$.

Each of these constructions therefore represents advantages.

The construction PAH-05/XG1 allows a choice of the colours desired at the end of the test, by having its thickness vary. However, it will not allow the "intensity" of the attack to be quantified since the final colours are the same.

The construction C5-XG1 reveals more clearly the enzymatic attack. In fact, the entire detection layer can be degraded when the conditions are combined, revealing incomplete attacks, by a change of colours in the detection layer.

In the two situations, detection is 50 times more sensitive than during testing according to Example 2.

Example 4

Enzymatic Activity Detection

Equipment

Complementary tests on enzymatic activity detection were run on devices including a detection layer deposited according to a protocol detailed in Example 1.

The two devices used, hereinafter designated $(C5-XG1)_5$ and $(C5-XG1)_8$, comprise a detection layer consisting respectively of 5 and 8 pairs of sub-layers.

Each pair of sub-layers comprises:
  a sub-layer of cellulose nanocrystals deposited at a concentration of 5 g/L, and
  a sub-layer of xyloglucane deposited at a concentration of 1 g/L.

The films present respectively:
  for the film $(C5-XG1)_5$, a brown colour and a thickness of around 70 nm, and
  for the film $(C5-XG1)_8$, a blue colour and a thickness of around 127.5 nm, with a standard variation of 3.28 nm.

The studied enzyme consists of a mixture of Cellulyve TR enzymes from the Lyven Company, consisting of a mixture of several cellulases, whose initial activity is 4880 nkat/g.

This enzyme solution is tested on two devices at the following respective concentrations: 100 mg/L, 50 mg/L, 25 mg/L, 20 mg/L, 15 mg/L, 10 mg/L, 1 mg/L and 0.1 mg/L.

Results

The 2 µL drops of enzymatic solutions at different concentrations are deposited on the detection layers which are put into an oven at 50° C. for 10, 30 and 60 minutes.

The appearance of the films $(C5-XG1)_5$ and $(C5/XG1)_5$ is compared before and after the enzymatic sensitivity test. Activity is detected when the colour of the detection layer is modified.

For the sample $(C5-XG1)_5$, after 10 minutes of reaction, the substrate is visible for concentrations of 100 mg/L and 50 mg/L, suggesting total degradation of the film. In addition, the colour of the film turns brown for some of the following lower concentrations, 25 mg/L, 20 mg/L and 15 mg/L, whereas it remains unchanged starting from a concentration of 10 mg/L.

After 30 minutes of reaction, the degradation of the sample $(C5-XG1)_5$, by enzyme solutions at concentrations of 15 and 10 mg/L, is clearly visible.

Increasing the reaction time to 60 minutes does not significantly improves detection in that the lowest concentrations (1 mg/L and 0.1 mg/L) do not always cause a change of colour.

Conversely, it is noteworthy that the degradation by the enzyme solution as a concentration of 10 mg/L is increased for 60 minutes of incubation compared to a 30 minute incubation time because the brown colour visible after 30 minutes is replaced by the grey colour of the substrate at 60 min.

Tests on the sample (C5-XG1)$_5$ reveal similar characteristics.

The only difference comes from the solution of enzymes at a concentration of 10 mg/L: degradation is complete for the sample (C5-XG1)$_5$ after 30 minutes whereas this degradation was only partial for the sample (C5-XG1)$_8$ as specified above.

These results reveal that the reaction time and the thickness of the film are important parameters for optimizing sensitivity and the response during testing.

In addition, the combination of the reaction time and the thickness of the detection layer are adjustable parameters for the semi-quantitative evaluation of the enzymatic activity. For instance, the enzyme solution whose concentration is 10 mg/L is not detected after 10 minutes of incubation but produces a positive result after 30 minutes of incubation (remember that partial degradation is obtained for the sample (C5-XG1)$_8$).

Example 5

Formulation and Degradation for Additional Biopolymers

To assess the application possibilities of the method according to the invention to other biopolymers, we have produced a summary evaluation of several biopolymer/enzyme couples, using the disappearance of the colour as confirmation of activity detection.

In conformity with Examples 1 to 3, deposits were made on silicon substrates having a higher refraction index than that of the biopolymer layer, in order to highlight the colours.

In each case, we use water and a thermally deactivated enzyme solution (the solution is brought to the boil for a few minutes then deposited) as references.

For all the results given below, the enzyme solutions, the deactivated enzyme and water solutions were incubated for 3 minutes at ambient temperature.

Deposit of Bovine Albumin Serum with Degradation by Trypsine.

The layer of bovine albumin serum was obtained by spin-layering a solution of 10 g/L containing 0.1 g/L of an MUF resin. The layer was reticulated at 90° C. for one hour.

Deposit of Bovine Albumin Serum Mixed with Chitosan, Degradation by Trypsine.

The layer of bovine albumin serum was obtained by spin-layering a solution of 10 g/L of BAS mixed with chitosan (10 g/L) to favour reticulation. The layer was immobilized by adding a 0.1 g/L solution of an MUF resin followed by reticulation for one hour at 90° C.

Deposit of Pectin and Degradation by a Pectinolytic Cocktail.

The layer of pectin was obtained by spin-layering a solution of 10 g/L containing 5% by weight of an MUF resin. The layer was reticulated at 90° C. for one hour.

Results:

In all three cases, up to incubation and rinsing, there is a change of colours only in the area where the active enzymes solution was deposited.

The invention claimed is:

1. A colorimetric device for detecting, in an aqueous solution of interest, a hydrolytic enzymatic activity capable of hydrolyzing at least one biopolymer of interest,
    which device comprises (i) a substrate delimited by at least one upper surface, and (ii) a transparent detection layer, having a first thickness and including said biopolymer, wherein said transparent detection layer includes an upper surface, for receiving said aqueous solution of interest and forming a first interface between the air and said detection layer, and a lower surface for forming a second interface between said detection layer and said substrate, wherein said first interface and said second interface are able to generate an optical interference,
    wherein said detection layer is adapted so that after application of said aqueous solution of interest, in the absence of said hydrolytic enzymatic activity, said detection layer preserves said first thickness, and after said application of said aqueous solution of interest, when said detection layer includes said hydrolytic enzymatic activity, said detection layer has a second thickness which is thinner than said first thickness,
    wherein said first thickness and/or said second thickness of said detection layer are adapted to generate a colour by an optical interference caused by the recombining of the light beams reflected at said first interface and at said second interface, and
    wherein said upper surface of said transparent detection layer is not covered by an additional nanoparticle layer.

2. The colorimetric device according to claim 1, wherein said first thickness of said detection layer is chosen to generate a first colour by an optical interference phenomenon, and wherein said detection layer is adapted so that, after application of said aqueous solution of interest, when said detection layer is deprived of the said hydrolytic enzymatic activity, said first thickness generating said first colour is preserved, and following said application of said aqueous solution of interest when said detection layer includes said hydrolytic enzymatic activity, said detection layer presents said second thickness, thinner than the first thickness, producing either a second colour by an optical interference phenomenon, different from said first colour, or causing said first colour to disappear.

3. The colorimetric device according to claim 1, wherein said first thickness of said transparent detection layer is a uniform thickness chosen from a range of thickness between 70 nm and 900 nm.

4. The colorimetric device according to claim 1, wherein said first thickness, said second thickness or both of the said transparent detection layer are adapted to generate a colour by an optical interference phenomenon with maximum reflectance for a wavelength between 380 nm and 780 nm.

5. The colorimetric device according to claim 1, wherein said transparent detection layer has a refractive index $n_c$ between 1.2 and 1.7.

6. The colorimetric device according to claim 1, wherein said transparent detection layer has a refractive index $n_c$ between 1.4 and 1.6.

7. The colorimetric device according to claim 1, wherein said substrate is transparent and said transparent detection layer has a refractive index $n_c$ which is different from the refractive index $n_s$ of said substrate.

8. The colorimetric device according to claim 1, wherein said substrate is opaque and has a reflecting upper surface.

9. The colorimetric device according to claim 1, characterized in that said biopolymer or biopolymers contained in said transparent detection layer is or are in an immobilized form.

10. The colorimetric device according to claim 9, wherein said transparent detection layer contains nanocrystals forming hydrogen cross-linked networks with said biopolymer or biopolymers of interest.

11. The colorimetric device according to claim 10, wherein said nanocrystals consist of polysaccharide nanocrystals.

12. The colorimetric device according to claim 10, wherein said nanocrystals consist of cellulose nanocrystals.

13. The colorimetric device according to claim 10, wherein said nanocrystals have a negative charge, and wherein said transparent detection layer consists of at least two sub-layers each containing said biopolymer of interest wherein said biopolymer sub-layers are separated in pairs by an interposed sub-layer containing a poly-cationic compound.

14. The colorimetric device according to claim 10, wherein said transparent detection layer consists of at least one pair of two sub-layers each containing at least one biopolymer of interest, with a first sub-layer having a first biopolymer or first biopolymers of interest and a second sub-layers containing a biopolymer polymer or second biopolymers of interest.

15. The colorimetric device according to claim 9, wherein said transparent detection layer contains a resin forming covalent cross-linked networks with said biopolymer or biopolymers of interest.

16. A process for detecting, in an aqueous solution of interest, hydrolytic enzymatic activity capable of hydrolysing to at least one biopolymer of interest; the method comprising the following succession of steps:
supplying said colorimetric device according to claim 1,
applying said aqueous solution of interest to said upper surface of said transparent detection layer,
washing of said upper surface of said transparent detection layer,
drying of said transparent detection layer, and
analysis of the colour of said transparent detection layer at the application site of said solution of interest.

17. The process of claim 16, wherein in said colorimetric device said first thickness of said detection layer is chosen to generate a first colour by an optical interference phenomenon, and wherein said detection layer is adapted so that, after application of said aqueous solution of interest, when it is deprived of said hydrolytic enzymatic activity, said first thickness generating said first colour is preserved; following said application of said aqueous solution of interest when said detection layer includes said hydrolytic enzymatic activity, said detection layer presents said second thickness, thinner than said first thickness, producing either a second colour by an optical interference phenomenon, different from said first colour, or causing said first colour to disappear.

18. The process of claim 16, wherein in said colorimetric device, said biopolymer or biopolymers contained in said transparent detection layer is or are in an immobilized form.

19. The process of claim 18, wherein in said colorimetric device, said transparent detection layer contains nanocrystals forming hydrogen cross-linked networks with said biopolymer or biopolymers of interest.

* * * * *